US009610060B2

(12) United States Patent
Jaeschke et al.

(10) Patent No.: US 9,610,060 B2
(45) Date of Patent: Apr. 4, 2017

(54) METHOD OF MONITORING A FETAL HEART RATE

(75) Inventors: Stefan Jaeschke, Stuttgart (DE); Markus Wohlschlager, Sindelfingen (DE); Hansjoerg Geywitz, Kusterdingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 2077 days.

(21) Appl. No.: 12/669,618

(22) PCT Filed: Jul. 21, 2008

(86) PCT No.: PCT/IB2008/052919
§ 371 (c)(1),
(2), (4) Date: Jan. 19, 2010

(87) PCT Pub. No.: WO2009/013701
PCT Pub. Date: Jan. 29, 2009

(65) Prior Publication Data
US 2010/0168596 A1  Jul. 1, 2010

(30) Foreign Application Priority Data
Jul. 24, 2007  (EP) ..................................... 07113011

(51) Int. Cl.
*A61B 8/00* (2006.01)
*A61B 8/08* (2006.01)
(Continued)

(52) U.S. Cl.
CPC ........ *A61B 8/0866* (2013.01); *A61B 5/02411* (2013.01); *A61B 8/02* (2013.01);
(Continued)

(58) Field of Classification Search
CPC .......................... A61B 8/0866; A61B 5/02411
(Continued)

(56) References Cited

U.S. PATENT DOCUMENTS

| 5,123,420 A | 6/1992 | Paret |
| 6,178,343 B1 | 1/2001 | Bindszus et al. |

(Continued)

FOREIGN PATENT DOCUMENTS

| DE | 2826391 | 1/1980 |
| EP | 0367251 | 5/1990 |

(Continued)

OTHER PUBLICATIONS

Van Leeuwen, P., et al.; Is there evidence of fetal-maternal heart rate synchronization?; 2003; BMC Physiology; vol. 3; pp. 1-11.

*Primary Examiner* — Edward Moran
*Assistant Examiner* — Nadia A Mahmood

(57) ABSTRACT

The invention relates to a method of monitoring a fetal heart rate, the method comprising: providing a first measurement head (104) and a second measurement head (106) and a sensor (200), the sensor (200) being comprised in the first measurement head (104) or the second measurement head (106), the sensor (200) being adapted to sense the maternal heart rate, the first measurement head (104) being adapted to sense maternal-fetal related medical data and the second measurement head (106) being adapted to sense the fetal heart rate, measuring the maternal heart rate by acquiring maternal heart rate data using the sensor (200), measuring the fetal heart rate by acquiring fetal heart rate data using the second measurement head (106), acquiring the maternal-fetal related medical data, detecting maternal-fetal heart rate coincidences by analyzing the maternal heart rate data and the fetal heart rate data.

13 Claims, 3 Drawing Sheets

(51) Int. Cl.
*A61B 5/024* (2006.01)
*A61B 8/02* (2006.01)
A61B 5/03 (2006.01)
A61B 5/053 (2006.01)
A61B 5/00 (2006.01)

(52) U.S. Cl.
CPC ........ *A61B 8/5276* (2013.01); *A61B 5/02416* (2013.01); *A61B 5/033* (2013.01); *A61B 5/0535* (2013.01); *A61B 5/721* (2013.01); *A61B 8/4472* (2013.01)

(58) Field of Classification Search
USPC .................................................. 600/511, 301
See application file for complete search history.

(56) References Cited

U.S. PATENT DOCUMENTS

| | | | |
|---|---|---|---|
| 6,740,033 B1* | 5/2004 | Olejniczak et al. | 600/301 |
| 6,751,498 B1* | 6/2004 | Greenberg et al. | 600/511 |
| 2004/0167381 A1 | 8/2004 | Lichter et al. | |
| 2004/0243015 A1 | 12/2004 | Smith et al. | |
| 2005/0199583 A1 | 9/2005 | Cohen et al. | |
| 2005/0267376 A1* | 12/2005 | Marossero et al. | 600/511 |
| 2005/0277841 A1 | 12/2005 | Shennib | |
| 2006/0229518 A1 | 10/2006 | Ofek | |
| 2007/0276251 A1* | 11/2007 | Orenstein et al. | 600/459 |

FOREIGN PATENT DOCUMENTS

| | | | |
|---|---|---|---|
| JP | 08000630 A | 1/1996 | |
| JP | 2002191570 A | 7/2002 | |
| JP | 2002532182 A | 10/2002 | |
| WO | 2005110236 A1 | 11/2005 | |

\* cited by examiner

METHOD OF MONITORING A FETAL HEART RATE

TECHNICAL FIELD

The invention relates to a method of monitoring a fetal heart rate, a measurement head and a computer program product.

BACKGROUND AND RELATED ART

Fetal monitors are devices for measurement visualization of one or more physiological parameters of unborn human beings. These monitors consist of multiple sensor elements for measuring uterine activity and one or more fetal heart rates. Basically two methods are used for electronic monitoring. The external or indirect method employs the use of external transducers placed on the maternal abdomen. Typically, ultrasound Doppler transducers are used in this category, where high frequency sound waves reflect mechanical action of the fetal heart. The internal or direct method uses a spiral electrode to receive a fetal electrocardiogram obtained from the presenting part of the unborn. This method can be used only when the presenting part is accessible and identifiable.

Monitors using ultrasound Doppler technologies normally accurately detect the fetal heart rate. However, electronic fetal monitors may unintentionally record maternal heart rate in the case of weak or absent fetal heart rate or if transducers are misplaced.

In addition to that, traces recorded with ultrasound Doppler can show the phenomenon of double counting. Double counting may occur if a maternal aortic wall movement during systole is nearly identical to the aortic wall movement during diastole. The envelope wave derived from the sensor signal then has identical shapes and the fetal monitor software cannot detect a difference between the two. Instead of counting a beat of the heart as one, two will be counted which can double the heart rate. Therewith, heart rate doubling occasionally occurs when measuring weak signals caused for example by aortic wall movements. Often the doubled maternal heart rate appears to have exaggerated variability and therefore may be interpreted as fetal heart rate.

Maternal heart rate patterns can mimic fetal heart rate patterns on such recordings. Misinterpreting a wrong heart rate trace may lead to unnecessary actions, unnecessary surgery, delayed delivery of a compromised fetus or even fetal death.

Because the fetal monitoring technology cannot detect the difference between a fetal and a maternal signal source when using fetal transducers, all fetal monitor manufacturers recommend producing a continuous maternal trace. Various techniques are known for this purpose. Firstly the pulse can be measured manually via stop watch. Secondly, the maternal heart rate may be obtained from a maternal pulse oximeter sensor placed on the maternal finger or ear. Thirdly, the application of the electrocardiogram device can be used to generate the maternal heart rate trace. Another possibility is to place a second ultrasound transducer over the maternal heart.

Therefore, most fetal monitors have built-in comparison algorithms for identifying identical fetal and maternal heart rates. The cross-channel verification feature helps detecting these trace coincidences. Question marks are automatically printed whenever two recorded heart rate traces show similarities over a certain amount of time.

US 2004/0243015 A1 discloses an apparatus for monitoring a fetal heart beat to extract one or more fetal electrocardiograms from a composite signal detected at the abdomen of a pregnant woman.

US 2005/0119583 A1 discloses a heart rate monitor apparatus and method.

US 2005/0267376 A1 discloses a maternal-fetal monitoring system for use during all stages of pregnancy.

US 2006/0229518 A1 discloses a method to analyze the fetus heart beat signal and detect a specific list of fetal heart rate arrhythmias in a non-intrusive, non-invasive and non-emitting way.

WO2005/110236 A1 discloses a beltless device for monitoring labor contractions via a fiber optic cable and fetal heart beats via an ultrasound sensor.

U.S. Pat. No. 6,178,343 discloses a pulse rate and heart rate coincidence detection unit for pulse oximetry.

State of the art methods to improve the fetal heart rate detection by additionally acquiring the maternal heart rate require either additional sensors or at least additional electrodes, which is a major disadvantage. Electrodes and sensors add additional cables, thus increasing patient's and caregiver's inconvenience. As a result, any method that adds additional sensors and/or electrodes is not well accepted.

SUMMARY OF THE INVENTION

The present invention provides a method of monitoring a fetal heart rate, the method comprising providing a first measurement head and a second measurement head and a sensor, the sensor being comprised in the first measurement head or the second measurement head, the sensor being adapted to sense the maternal heart rate, the first measurement head being adapted to sense maternal-fetal related medical data and the second measurement head being adapted to sense the fetal heart rate. The method further comprises measuring the maternal heart rate, measuring the fetal heart rate, acquiring the maternal-fetal related medical data and detecting maternal-fetal heart rate coincidences by analyzing the maternal heart rate and the fetal heart rate.

The method according to the invention has the advantage that the sensor can be invisibly integrated into any existing measurement head. Since the sensor can be simply placed into an existing sensor housing, no additional cables or sensors are required. The general handling of the sensors does not change, so caregivers do not need further training. This will clearly improve the acceptance in labor rooms.

By automatically measuring in parallel the maternal heart rate and the fetal heart rate, the risk of trace misinterpretation is reduced. Also, measuring the maternal heart rate does not require any additional disposables as necessary for ECG measurement and no extra training of caregivers is necessary, which means that the acceptance in clinics will be high.

In accordance with an embodiment of the invention, the method further comprises artifact detection and correction of the maternal heart rate data, wherein the detection and correction is performed for example by analyzing the maternal-fetal related medical data. Further, the correction comprises motion artifact correction. Thereby, the artifact correction is performed preferably on the raw data acquired by measuring the maternal heart rate.

By implementing an artifact correction of the maternal heart rate data, the robustness of the heart rate detection algorithm is increased. This is crucial for the detection of trace coincidences and thus for reliable fetal monitoring Artifacts occurring during the measurement of the maternal heart rate may arise for example due to patient breathing or patient motion, or even motion of the fetus within the uterus of the patient. In case the first measurement head is adapted to sense any kind of spatial variations of the abdominal wall or comprises a motion sensitive sensor, by analyzing the maternal-fetal related medical data acquired by the first measurement head it is possible to accurately correct signal variations resulting from said motion artifacts.

Further, in case the sensor is an optical sensor it is possible to correct strong external light incidences with means of a respective artifact correcting algorithm. Such algorithms may for example comprise a correction due to strong deviations from the measured maternal heart rate signal acquired by the sensor. Typically, heart rate measurements show a periodic, regular reoccurrence of heart pulses such that a sudden strong light incidence causing irregular strong peaks in the detected measured maternal heart rate can be easily filtered out.

In accordance with an embodiment of the invention the method further comprises transmitting of the maternal heart rate, the fetal heart rate and the maternal-fetal related medical data to a display unit, for example to a fetal monitor or directly to a clinical data management system, e.g. TraceVue. Thereby, the transmission is performed with means of a wireless and/or a wired connection. By integrating the sensor into the first or second measurement head, a sensor with small size and low power consumption is ideally suited for integration in measurement heads of wireless fetal transducers.

Regarding the connection of the first or the second measurement head with the integrated sensor to the display unit, only the transmission interface of the first or second measurement head has to be adapted accordingly in order to be able to transmit the sensor signal additionally with data acquired with the first or second measurement head itself.

In accordance with an embodiment of the invention, the sensor is adapted as a plethysmography electrode, wherein the plethysmography electrode is a bio-impedance and/or optical based electrode, wherein for a bio-impedance based electrode said electrode is adapted for capacitive and/or galvanic tissue electrode coupling. Thereby, the sensor can be additionally adapted for impedance measurement at various measurement frequencies. In this case, the method further comprises using of phase sensitive detection means. In case of a galvanic tissue electrode coupling, a galvanic insulation between the patient and the measurement device has to be ensured.

Especially the usage of optical based electrodes has the advantage that such kind of electrodes can be for example invisibly integrated into existing measurement head housings—the optical based electrode can be integrated into a measurement housing for example hidden behind a transparent transducer already built in the measurement housing. Transparent in this context has to be understood as at least partially permeable to the wavelength of light used by the optical based electrode.

By using the measurement head with the hidden additional integrated optical sensor, caregivers and patients can benefit from additional information regarding maternal-fetal heart rates without applying any change to the common state of the art procedure of acquiring maternal-fetal related medical information. The apparent number of applied transducers is the same as for state of the art systems using only a measurement head and a second sensor separated from the measurement head to detect the fetal heart rate, which is important that this method is accepted by caregivers and patients.

It has to be mentioned, that it is also possible to integrate multiple sensors, in particular optical sensors in a measurement head. This has the advantage, that measurement signals from these multiple sensors can be used to significantly reduce the breakdown susceptibility of a maternal and thus fetal heart rate measurement. However, this advantage can be gained without any additional cable cluttering and any additional sensor placement steps on the maternal body. Therewith, the patient safety is enhanced while the patient and caregivers comforts are maintained.

It should further be mentioned, that the sensor for detecting the maternal heart rate can be integrated into any kind of measurement head which is carried close to the maternal body.

In accordance with an embodiment of the invention, the second measurement head comprises an ultrasound sensor or a direct electrocardiogram sensor or an abdominal electrocardiogram sensor or an acoustic sensor.

In accordance with an embodiment of the invention, the first measurement head is a tocodynamometer or signal processing unit of an intra uterine pressure sensor. Placing for example an optical sensor into the tocodynamometer (TOCO) housing has various advantages for more effective signal processing. The TOCO sensor records the labor activity by measuring pressure changes at a maternal abdomen. The same technique can be used to detect maternal breathing and motion artifacts as already mentioned above, which also effects the optical measurement. Using these two different measurement sources, the artifact resistance can be increased for a higher liability and reliability of the measured maternal heart rate.

In another aspect, the invention relates to a measurement head comprising means for acquiring maternal-fetal related medical data and a sensor adapted for acquiring a maternal heart rate, as well as means for transmitting the acquired maternal-fetal related medical data and the acquired maternal heart rate to a data processing unit.

In another aspect, the invention relates to a measurement head comprising means for sensing a fetal heart rate, and a sensor adapted for acquiring a maternal heart rate, as well as means for transmitting the acquired fetal heart rate and the acquired maternal heart rate to a data processing unit.

Due to the common size of measurement heads for acquiring maternal-fetal related medical data or fetal heart rates, especially in case of tocodynamometers and ultrasound transducers, a photoplethysmographic sensor can be easily integrated in the existing housing of said transducer.

Also, by using a tocodynamometer or ultrasonic transducer, the press-on force of the tocodynamometer or the ultrasonic sensor on the maternal skin is limited and well defined due to the rather large respective sensor surfaces. Therewith, also a well defined press-on force of the photoplethysmographic sensor being integrated in one of the sensors ensures a well defined interaction between the photoplethysmographic sensor and the maternal skin. This facilitates the usage of the photoplethysmographic sensor and sophisticated arrangements of ECG electrodes or pulse oximeter sensors can be avoided.

This ensures a possibility to monitor reliably the fetal heart rate, even for care givers with rather low technical and medical skills that operate a measurement head according to the invention.

In accordance with an embodiment of the invention, the measurement head further comprises means for motion artifact correction. However, it has to be noted that a motion artifact correction, as well as any kind of signal processing with respect to data signals being recorded by the measurement head can be also performed externally in the data processing unit.

In accordance with an embodiment of the invention, the data processing unit is adapted as a display unit. Thereby, this display unit is adapted as known in the art to display the maternal heart rate together with additionally acquired information regarding the fetal heart rate and to detect maternal-fetal heart rate coincidences by analyzing the maternal heart rate and the fetal heart rate.

In accordance with an embodiment of the invention, the sensor is adapted as a plethysmography electrode, wherein the plethysmography electrode is a bio-impedance electrode, wherein said electrode is adapted for capacitive and/or galvanic tissue electrode coupling.

In accordance with an embodiment of the invention, the sensor is adapted as an optical based electrode. Thereby, the measurement head is adapted to be placed on the skin surface, especially the abdominal wall of the patient. Since in this case the measurement head comprises an interface layer to be applied to said skin surface, the interface layer is preferably permeable to light being used for operation of the optical based electrode. This is easily realizable in case of a tocodynamometer, since the strain gage used for measuring pressure changes at the maternal abdomen can be adapted to be transparent for e.g. infrared light or other suitable light wavelengths. Therewith, the optical photoplethysmographic sensor can be simply integrated in the existing housing of a tocodynamometer transducer and this additional sensor will be completely invisible for caregivers and patients.

In another aspect, the invention relates to a computer program product comprising computer executable instructions for performing the method of the invention.

BRIEF DESCRIPTION OF THE DRAWINGS

In the following preferred embodiments of the invention are described in greater detail by way of example only making reference to the drawings in which.

DETAILED DESCRIPTION

Figure 1:
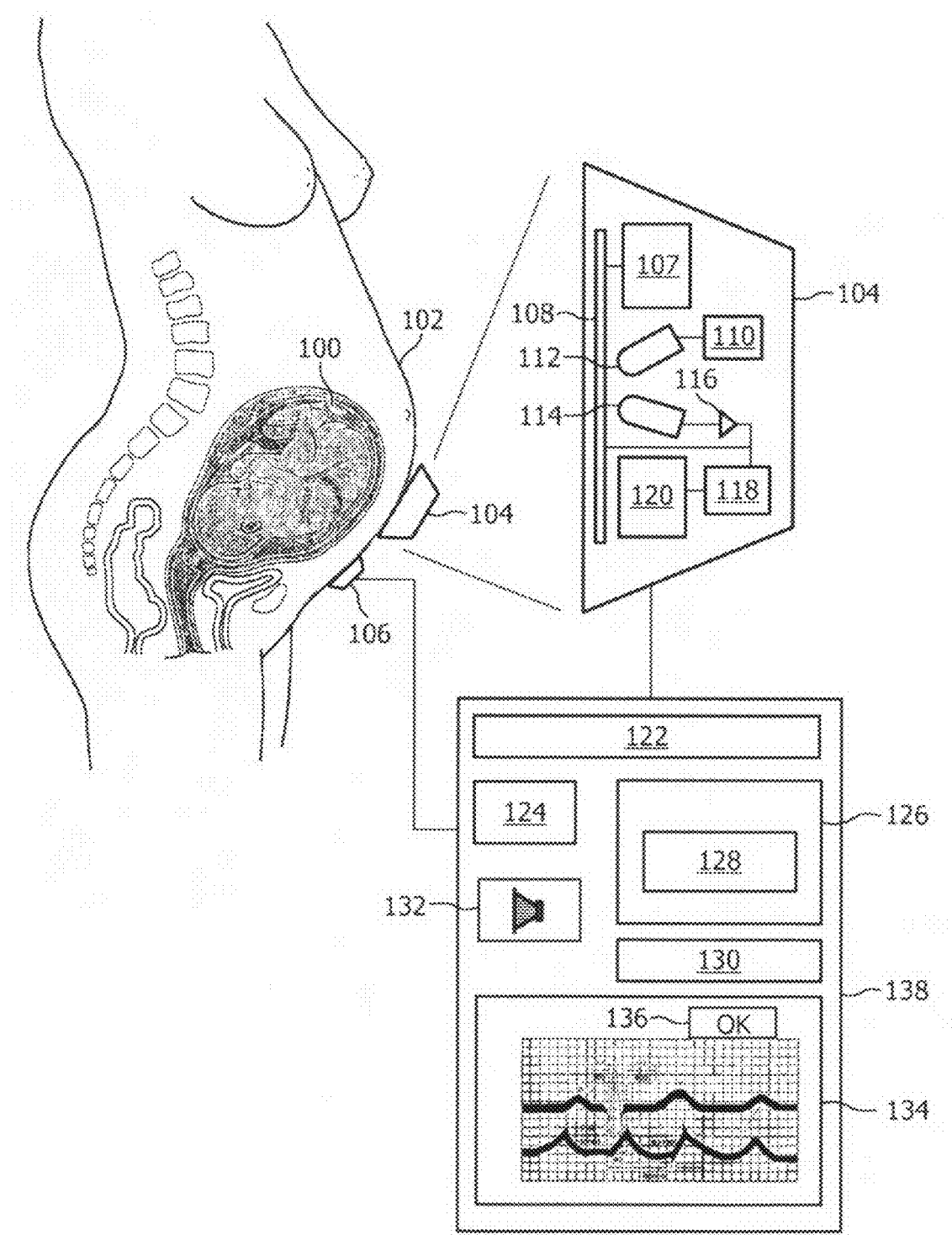
FIG. 1: shows a block diagram of an embodiment of a tocodynamometer with an integrated photoplethysmographic sensor positioned on a woman's abdomen.

In the following, similar elements are designated by the same reference numerals.

FIG. 1 shows a block diagram of an embodiment of a tocodynamometer (TOCO) 104 with an integrated photoplethysmographic sensor 112, 114 positioned on a woman's abdomen 102. Thereby, the TOCO 104 comprises as known in the art a respective sensor 108 to measure pressure changes of the maternal abdomen 102. The sensor 108 is controlled by a control unit 107.

The photoplethysmographic sensor comprised in the TOCO 104 consists mainly of a light source 112 and an optical receiver 114. The light source 112 is preferably an infrared LED. Light source 112 and optical receiver 114 are arranged in a reflective sensor array. The receiver 114 detects the changes of the reflected light caused by a blood pulse in the arterial vessels of the maternal abdomen 102. Thereby, the blood pulse directly corresponds to the maternal heart rate. Due to the optical measurement method a misleading recording of the fetal heart rate is excluded, since the penetration depth of the light waves is only a few millimeters.

The light source 112 is controlled by a control unit 110 and the detected infrared light detected by the optical receiver 114 is amplified using an amplifier 116. The amplified light signal is input to a signal processing unit 118, which also allows for artifact suppression of for example maternal breathing and motion artifacts. In order to perform such an artifact suppression, the measurement results obtained with means of the sensor 108 which is sensitive to pressure and therewith motion changes at the maternal abdomen can be additionally used.

The measured pressure changes acquired with means of the sensor 108, as well as the detected maternal heart rate are transmitted with means of an interface 120 to a fetal monitor 138. The fetal monitor 138 also comprises an interface 122 to receive information from the TOCO 104 and a further sensor 106. Thereby, the sensor 106 may be either an internal (direct ECG) or external sensor, like an ultrasound transducer. The sensor 106 is thereby adapted to acquire the heart rate of the fetus 100.

The fetal monitor 138 further comprises a processor 124 and a memory 126. The memory 126 comprises a module 128 comprising computer executable instructions. The module 128 can thereby be used for example to detect maternal-fetal heart rate coincidences by analyzing the maternal heart rate transmitted from the TOCO 104 with its integrated photoplethysmographic sensor, and the fetal heart rate transmitted from the ultrasound transducer 106.

The fetal monitor 138 further comprises input means 130, like a keyboard, a mouse, a touch screen or respective buttons to operate the fetal monitor 138.

The fetal monitor 138 further comprises a display 134. Thereby, the display 134 is adapted to display the maternal heart rate and the fetal heart rate. In the present example, the electrocardiograms displayed in the display 134 are obviously not related to each other. In this example the module 128 analyzes that the respective maternal heart rate and fetal heart rate do not coincide and therefore an 'ok' is displayed in a display element 136 of the display 134.

However, in case that the fetal monitor with its module 128 detects that the maternal and fetal heart rate coincide, multiple kinds of actions may be performed by the fetal monitor 138. For example, as known in the art question marks can be automatically printed whenever two recorded heart rate traces show similarities over a certain amount of time. It is also possible to signal a certain sound or signal any kind of optical hint with means of the signaling unit 132 to an operator using the fetal monitor 138.

In case of the occurrence of an optical hint, for example a blinking LED, an operator may be additionally indicated to perform several actions proposed by the fetal monitor 138. For example, the operator may be advised to reposition the ultrasound transducer 106. Such an advice can be given by the fetal monitor 138 for example, if the module 128 calculates with a high probability that the fetal heart rate signal detected by the ultrasound transducer 106 is still weakly detectable, however, a rearrangement of the ultrasound transducer 106 is supposed to improve the fetal heart rate signal to a desired value. Since the ultrasound transducer 112 requires acoustical coupling gel and frequent repositioning, such a repositioning procedure does not correspond to a life threatening situation. Therewith, in case such a simple repositioning of the sensor 106 would solve the problem, the simple optical hint on the display 134 could be sufficient to advise a caregiver to reposition the sensor 106 to a more appropriate position.

However, if in contrary the fetal heart rate signal suddenly disappears, fetal movements are probable, but in the worst case even a cardiac arrest of the fetus 100 is possible. In this case, the fetal monitor 138 may sound a special signal and display respective information on the display 134.

Due to the optical based measurement method of the maternal pulse rate, accidentally measuring the fetal heart rate is impossible. Continuous cross-channel verification reduces the risk of misinterpreting the maternal heart rate as the fetal heart rate. Therewith, the clinical staff is supported and the reliability of fetal monitoring is significantly increased and the risk of intrapartum fetal impairment and mortality is reduced.

Figure 2:
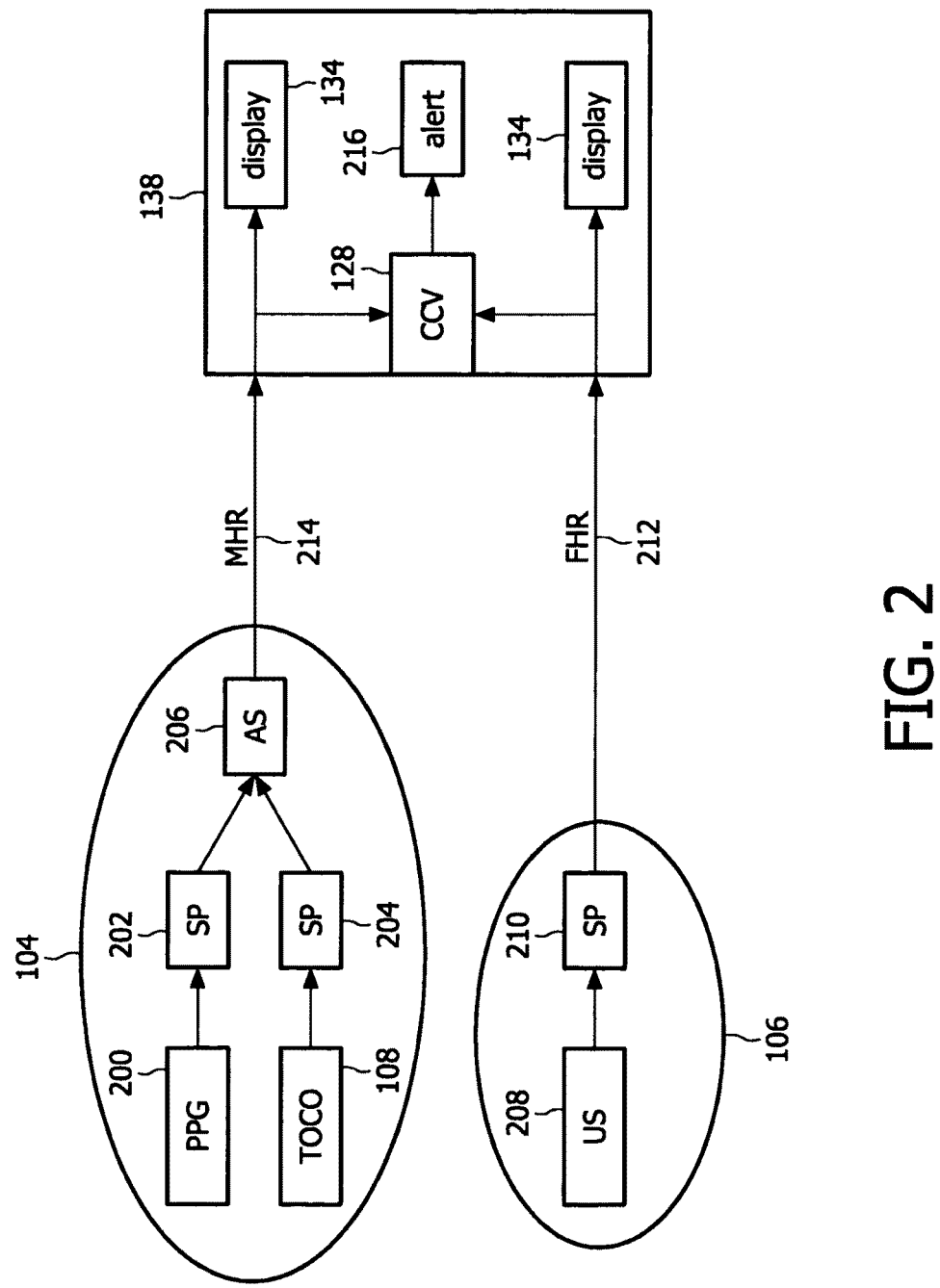
FIG. 2: shows a further block diagram of an embodiment of a measurement head comprising a sensor for measuring a maternal heart rate.

FIG. 2 shows a further block diagram of an embodiment of a measurement head 104 comprising a sensor 200 for measuring a maternal heart rate. The measurement head 104 comprises a TOCO transducer 108, as well as a photoplethysmographic sensor 200. Since the strain gage of the TOCO transducer 108 can be adapted in a way being permeable to the light being used for operation of the photoplethysmographic sensor 200, it is possible to invisibly integrate the photoplethysmographic sensor 200 into a common TOCO transducer measurement head with only a slight modification of the interface being used to transmit the data acquired with the TOCO transducer 108 together with the data acquired by the photoplethysmographic sensor 200 to the fetal monitor 138.

Even though, in the present example the strain gage of the TOCO transducer 108 is adapted in a way being permeable to the light being used for operation of the photoplethysmographic sensor 200, it is also possible to arrange the photoplethysmographic sensor 200 peripheral to the strain gage of the TOCO transducer 108.

The data acquired with the TOCO transducer 108, as well as data acquired with the photoplethysmographic sensor 200 are processed with respective signal processing units 204 and 202, respectively. The processed signals are then input into an artifact suppression unit 206. Therewith, placing the optical sensor into the housing of the TOCO sensor provides further possibilities for signal processing, such as motion and breathing artifact detection and suppression, and the robustness of the heart rate detection algorithm is significantly increased.

Finally, the artifact suppressed maternal heart rate signal is transmitted wired or wireless, eventually together with the data acquired by the TOCO transducer 108 to the fetal monitor 138.

Regarding the ultrasound sensor unit 106, the built-in ultrasound transducer 208 is used to detect and monitor a fetal heart rate. The detected fetal heart rate signal is processed using a signal processing unit 210 and transmitted to the fetal monitor 138 with means of a respective wireless or wired transmission line 212. Using the module 128, the fetal monitor 138 detects maternal-fetal heart rate coincidences by analyzing the maternal heart rate provided by the measurement head 104 and the fetal heart rate provided by the ultrasound sensor unit 106. The fetal heart rate as well as the maternal heart rate are both displayed together on the display unit 134. In case a coincidence between the maternal heart rate and the fetal heart rate occurs, the fetal monitor 138 generates an alert 216 to a user of the fetal monitor 138. Such an alert may be for example a sound signal and/or an optical signal, like a blinking LED, question marks on the display, advices to a user displayed on the display 134 and many more.

It has to be mentioned, that common state of the art fetal monitors 138 often already comprise such features of displaying the fetal and maternal heart rate in parallel, as well as to analyze the fetal and maternal heart rate regarding possible coincidences and to produce respective alert outputs. However, the disadvantage with such kinds of fetal monitors is, that they require additional sensor input for example from a maternal pulse oximeter sensor placed on the maternal finger. However, with the already built-in functionalities, a state of the art fetal monitor 138 may be upgraded by redefining the interface of such a fetal monitor 138 to allow communication with a new measurement head 104 according to the invention.

It further has to be mentioned, that the module 128 which is adapted for detecting of maternal-fetal heart rate coincidences can be a module comprised in the measurement head 104 or in the ultrasound sensor unit 106 or in the fetal monitor 138.

Figure 3:
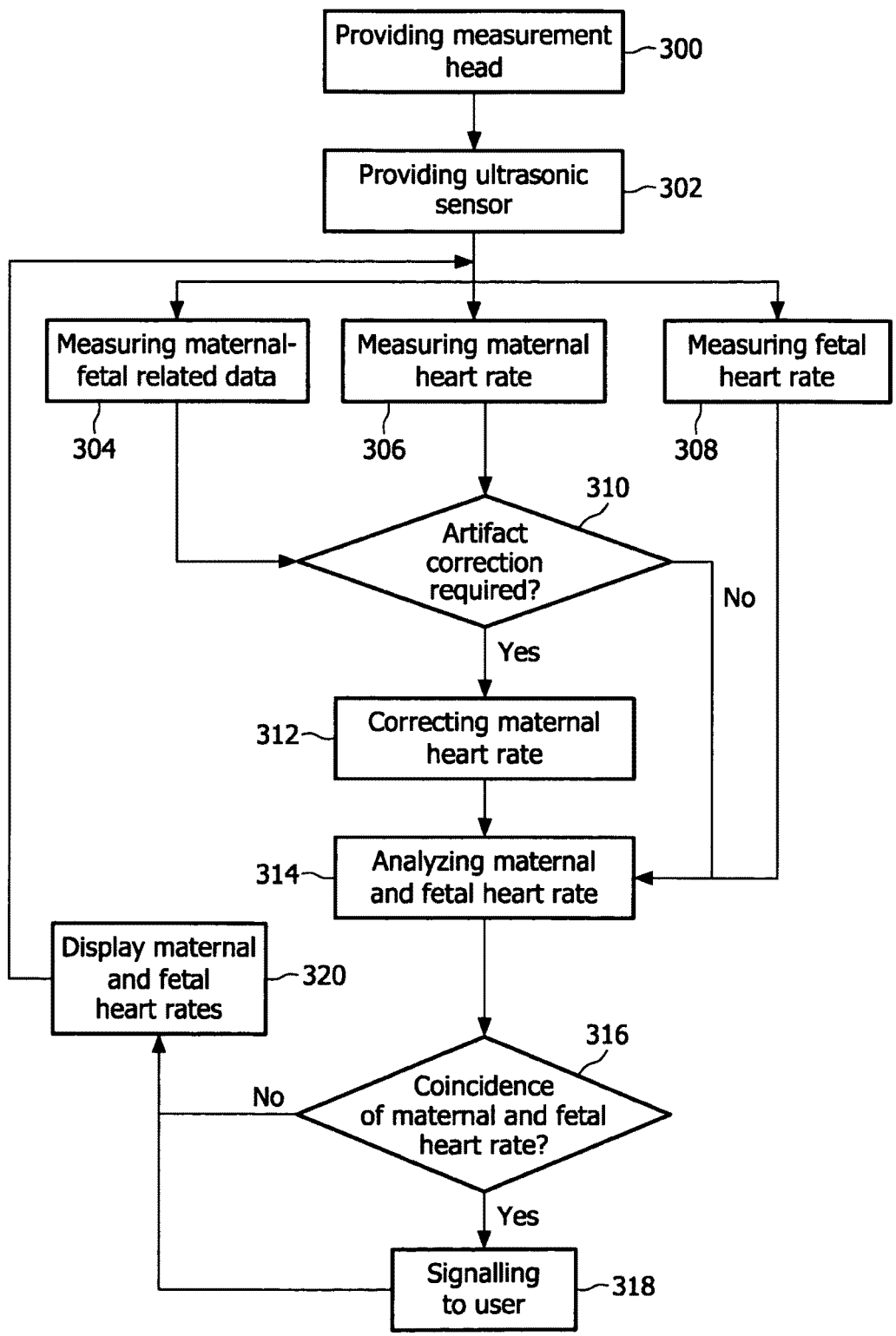
FIG. 3: shows a flowchart illustrating the method according to the invention to monitor a fetal heart rate.

FIG. 3 shows a flowchart illustrating the method according to the invention to monitor a fetal heart rate. In step 300, a measurement head is provided and in step 302 an ultrasonic sensor is provided. Intrapartum monitoring always requires two transducers, typically the ultrasound transducer and the TOCO transducer which are positioned individually on the mother's abdomen. According to the invention, the measurement head comprises besides a TOCO transducer an additional photoplethysmographic sensor in order to acquire the maternal heart rate.

After providing the measurement head and providing the ultrasonic sensor in step 300 and 302, the maternal heart rate is measured in step 306. In parallel to the measurement step 306, a measurement of the fetal heart rate is performed in step 308 using the ultrasound sensor. Further, also in parallel to the measurement step 306 a measurement of maternal-fetal related data is performed in step 304. In case a TOCO transducer is used for step 304, the maternal-fetal related data comprise information about the maternal uterine contractions.

The measured maternal-fetal related data of step 304 and the measured maternal heart rate of step 306 are analyzed in step 310 to determine if a an artifact correction in the maternal heart rate data is required. Such a maternal heart rate artifact correction may be required, if the measured maternal heart rate signal from step 306 comprises maternal breathing and motion artifacts, or optical scattering artifacts. In case in step 310 such a (raw data) correction is required, the correction is performed in step 312.

Either after step 310 or after step 312, the (corrected) maternal heart rate and the fetal heart rate from step 308 are analyzed in step 314. In case in step 316 the analysis yields that a coincidence of the maternal and fetal heart rate exists, a respective signaling is provided to the user in step 318.

Either after step 318 or in case a maternal-fetal heart rate coincidence is not detected in step 316, the maternal and fetal heart rates are displayed on a fetal monitor in step 320. After step 320, the procedure is continued and continuously repeated with steps 304, 306 and 308.

| LIST OF REFERENCE NUMERALS | |
| --- | --- |
| 100 | fetus |
| 102 | abdomen |
| 104 | measurement head |
| 106 | sensor |
| 107 | control unit |
| 108 | sensor |

-continued

| LIST OF REFERENCE NUMERALS | |
|---|---|
| 110 | control unit |
| 112 | LED |
| 114 | optical receiver |
| 116 | amplifier |
| 118 | signal processing unit |
| 120 | interface |
| 122 | interface |
| 124 | processor |
| 126 | memory |
| 128 | module |
| 130 | input means |
| 132 | signaling unit |
| 134 | display |
| 136 | display element |
| 138 | fetal monitor |
| 200 | PPG sensor |
| 202 | signal processing unit |
| 204 | signal processing unit |
| 206 | artifact suppression unit |
| 208 | ultrasound sensor |
| 210 | signal processing unit |
| 212 | connection |
| 214 | connection |

The invention claimed is:

1. A method of monitoring a fetal heart rate, the method comprising:
    providing a first measurement head and a second measurement head and a sensor, the sensor being included in the first measurement head or the second measurement head, the sensor configured to sense the maternal heart rate, the first measurement head configured to sense maternal-fetal related medical data and the second measurement head configured to sense the fetal heart rate,
    measuring the maternal heart rate by acquiring maternal heart rate data using the sensor,
    detecting artifacts and correcting the maternal heart rate data,
    measuring the fetal heart rate by acquiring fetal heart rate data using the second measurement head,
    acquiring the maternal-fetal related medical data,
    detecting maternal-fetal heart beat coincidences using the corrected maternal heart rate data and the fetal heart rate data.

2. The method of claim 1, wherein the correction includes motion artifact correction.

3. The method of claim 1, further including:
    transmitting of the maternal heart rate data, the fetal heart rate data and the maternal-fetal related medical data to a display unit.

4. The method of claim 3, wherein the transmission is performed with a wireless and/or a wired connection.

5. A measurement head including:
    a first sensor configured to acquire maternal-fetal related medical data,
    a second sensor configured to acquire maternal heart rate data,
    a module for artifact detection and correction of the maternal heart rate data, and
    a unit configured to transmit the acquired maternal-fetal related medical data and the acquired maternal heart rate data to a data processing unit.

6. The measurement head of claim 5, wherein the module for artifact detection and correction of the maternal heart rate data are configured to analyze the maternal-fetal related medical data.

7. A measurement head comprising:
    a first sensor configured to acquire maternal-fetal related medical data,
    a second sensor configured to acquire maternal heart rate data, wherein the second sensor includes a plethysmography electrode, wherein the plethysmography electrode is a bio-impedance electrode, wherein said electrode is configured for capacitive and/or galvanic tissue-electrode coupling,
    a unit configured to transmit the acquired maternal-fetal related medical data and the acquired maternal heart rate data to a data processing unit.

8. The measurement head of claim 7, wherein the sensor is configured for impedance measurements at various measurement frequencies.

9. The measurement head of claim 7, further including a phase sensitive detection module configured to detect an impedance measurement at various measurement frequencies.

10. The measurement head of claim 7, wherein the first sensor is an optical based electrode.

11. The measurement head of claim 10, wherein the measurement head is configured to be placed on the skin surface.

12. The measurement head of claim 11, wherein the measurement head includes:
    an interface layer to be applied to the skin surface, the interface layer being permeable to light being used for operation of the optical based electrode.

13. A non-transitory computer readable medium comprising computer executable instructions for performing the method of claim 1.

* * * * *